United States Patent
Hishinuma et al.

(10) Patent No.: US 11,047,720 B2
(45) Date of Patent: Jun. 29, 2021

(54) GAS METER SYSTEM AND HEATING VALUE ESTIMATION METHOD

(71) Applicant: TOKYO GAS CO., Ltd., Minato-ku (JP)

(72) Inventors: Masakazu Hishinuma, Tokyo (JP); Kenchi Kobayashi, Tokyo (JP)

(73) Assignee: TOKYO GAS CO., Ltd., Minato-ku (JP)

( * ) Notice: Subject to any disclaimer, the term of this patent is extended or adjusted under 35 U.S.C. 154(b) by 563 days.

(21) Appl. No.: 15/567,384

(22) PCT Filed: Mar. 11, 2016

(86) PCT No.: PCT/JP2016/057791
§ 371 (c)(1),
(2) Date: Oct. 18, 2017

(87) PCT Pub. No.: WO2016/170870
PCT Pub. Date: Oct. 27, 2016

(65) Prior Publication Data
US 2018/0128666 A1    May 10, 2018

(30) Foreign Application Priority Data
Apr. 23, 2015 (JP) .............................. JP2015-088777

(51) Int. Cl.
*G01F 3/22* (2006.01)
*G01F 1/66* (2006.01)
(Continued)

(52) U.S. Cl.
CPC ................ *G01F 1/66* (2013.01); *F17D 3/18* (2013.01); *G01F 3/22* (2013.01); *G01F 15/043* (2013.01);
(Continued)

(58) Field of Classification Search
CPC ........ G01F 1/66; G01F 15/043; G01F 15/063; G01F 3/22; G01N 29/024; G01N 33/225; F17D 3/18
See application file for complete search history.

(56) References Cited

U.S. PATENT DOCUMENTS 3,177,714 A    4/1965  Mayeran
5,816,705 A *  10/1998  Vander Heyden ..... G01N 25/22
374/37
(Continued)

FOREIGN PATENT DOCUMENTS

CN          1436296 A      8/2003
CN          100472172 C    3/2009
(Continued)

OTHER PUBLICATIONS

English translation of the International Preliminary Report on Patentability and Written Opinion dated Nov. 2, 2017 in PCT/JP2016/057791.
(Continued)

*Primary Examiner* — Mohamed Charioui
*Assistant Examiner* — Christine Y Liao
(74) *Attorney, Agent, or Firm* — Oblon, McClelland, Maier & Neustadt, L.L.P.

(57) ABSTRACT

A gas meter system is configured to: derive a unit heating value of a gas passing through a first gas meter; and estimate a heating value of a gas passing through a second gas meter provided separately from the first gas meter based on the heating value of the gas of the first gas meter that is arranged within a predetermined range with respect to the second gas meter on a gas supply pipe configured to supply the gas. The gas meter system and a heating value estimation method can estimate a heating value of a gas with high accuracy.

18 Claims, 9 Drawing Sheets

(51) Int. Cl.
*G01N 29/024* (2006.01)
*G01N 33/22* (2006.01)
*F17D 3/18* (2006.01)
*G01F 15/04* (2006.01)
*G01F 15/06* (2006.01)

(52) U.S. Cl.
CPC ......... *G01F 15/063* (2013.01); *G01N 29/024* (2013.01); *G01N 33/225* (2013.01)

(56) References Cited

U.S. PATENT DOCUMENTS

| | | | |
|---|---|---|---|
| 6,047,589 A | 4/2000 | Hammond et al. | |
| 6,330,831 B1 | 12/2001 | Lynnworth et al. | |
| 6,517,237 B1* | 2/2003 | Hammond | G01F 1/66 374/31 |
| 7,274,996 B2 | 9/2007 | Lapinski et al. | |
| 2004/0030520 A1 | 2/2004 | Matter et al. | |
| 2015/0245248 A1* | 8/2015 | Shudark | H04W 40/244 370/235 |
| 2015/0323364 A1* | 11/2015 | Sakaguchi | G01F 1/66 73/196 |

FOREIGN PATENT DOCUMENTS

| | | |
|---|---|---|
| CN | 202648859 U | 1/2013 |
| EP | 1 164 361 A1 | 12/2001 |
| JP | 3611416 B2 | 1/2005 |
| JP | 4903573 B2 | 3/2012 |
| JP | 2013-210344 A | 10/2013 |
| WO | WO 00/11465 A1 | 3/2000 |
| WO | WO 00/23773 A2 | 4/2000 |
| WO | 2005/042984 A2 | 5/2005 |

OTHER PUBLICATIONS

International Search Report dated Apr. 26, 2016 in PCT/JP2016/057791, filed on Mar. 11, 2016.

Office Action dated Apr. 20, 2018 in European Patent Application No. 16782892.0, 5 pages.

Supplementary European Search Report dated Apr. 10, 2018 in European Patent Application No. 16782892.0, 3 pages.

Combined Chinese Office Action and Search Report dated Mar. 6, 2019 in Patent Application No. 201680023013.8 (with unedited computer generated English translation of the Office Action and English Translation of Category of Cited Documents), 13 pages.

* cited by examiner

GAS METER SYSTEM AND HEATING VALUE ESTIMATION METHOD

TECHNICAL FIELD

The present invention relates to a gas meter system and a heating value estimation method for deriving a heating value of a gas.

BACKGROUND ART

In order for a gas utility to know a passage volume of a hydrocarbon gas consumed by a customer, the gas utility arranges a gas meter at a demand place to charge fees based on the passage volume of the gas, which is measured by the gas meter. In this case, when the gas supplied to the demand place has a constant heating value per unit volume, a passage heating value of the gas that has passed through the gas meter, that is, a gross heating value of the gas consumed by the customer can be accurately derived based on the passage volume of the gas. Therefore, the fees can be appropriately charged.

However, when the gas transmission side does not adjust the composition of the gas, gases having different gas compositions and thus having different heating values, which vary depending on time and location, may be supplied to the demand place. In such a case, it is difficult for a related-art gas meter configured to measure only the passage volume of the gas to accurately derive the passage heating value based on the usage amount of the gas, and fees may not be appropriately charged.

In view of this, there has been proposed a gas meter configured to, on the assumption that the gas to be supplied to the demand place is a hydrocarbon gas, measure a temperature and a sound velocity of the gas, estimate the heating value in a standard state of the gas based on the measured temperature and sound velocity, and derive the passage heating value based on the estimated heating value in the standard state, the passage volume of the gas, and the temperature of the gas (for example, Patent Literature 1).

CITATION LIST

Patent Literature

[PTL 1] Japanese Patent Application Laid-Open No. 2013-210344

SUMMARY OF INVENTION

Technical Problem

Incidentally, when a gas utility switches a related-art gas meter system in which fees are charged based on the passage volume to a gas meter system in which fees are charged based on the heating value and the passage volume, the gas utility is required to replace a gas meter configured to measure the usage amount of the gas with a gas meter capable of deriving the passage heating value.

However, it is difficult to replace all of the gas meters at once at the same timing, and there is a period in which the gas meter configured to measure the usage amount of the gas and the gas meter capable of deriving the passage heating value are mixed. In such a case, inequality in fees may occur between a customer charged based on the passage volume of the gas and a customer charged based on the passage heating value and the passage volume.

In view of this, in an area (gas supply pipeline network) in which the gas meter configured to measure the passage volume of the gas and the gas meter capable of deriving the heating value are installed in a mixed manner, fees may be charged with use of an average heating value in the area. However, the average heating value may differ from the heating value of the gas that is actually used, and thus the inequality is not solved.

The present invention has been made in view of the above-mentioned problem, and has an object to provide a gas meter system and a heating value estimation method that are capable of estimating a heating value of a gas with high accuracy in a gas meter capable of measuring only a flow rate of the gas.

Solution to Problem

In order to solve the above-mentioned problem, according to one embodiment of the present invention, there is provided a gas meter system including: a heating value derivation unit configured to derive a heating value of a gas passing through a first gas meter; and a heating value estimation unit configured to estimate a heating value of a gas passing through a second gas meter provided separately from the first gas meter based on the heating value of the gas of the first gas meter that is arranged within a predetermined range with respect to the second gas meter on a gas supply pipe configured to supply the gas.

Further, it is preferred that the gas meter system further include a sound velocity derivation unit configured to derive a sound velocity of the gas supplied to the first gas meter, and that the heating value derivation unit be configured to derive the heating value of the gas passing through the first gas meter based on the sound velocity of the gas, which is derived by the sound velocity derivation unit.

Further, it is preferred that the gas be a hydrocarbon gas.

Further, it is preferred that the gas meter system further include a temperature sensor configured to measure a temperature of the gas supplied to the first gas meter, and that the heating value derivation unit be configured to derive the heating value of the gas passing through the first gas meter based on the sound velocity of the gas, which is derived by the sound velocity derivation unit, and on the temperature of the gas, which is derived by the temperature sensor.

Further, it is preferred that the gas meter system further include an abnormality diagnosis unit configured to diagnose whether or not a present heating value is abnormal based on transition of the heating value, which is derived by the heating value derivation unit.

Further, according to one embodiment of the present invention, there is provided a heating value estimation method including: deriving a heating value of a gas passing through a first gas meter; and estimating a heating value of a gas passing through a second gas meter provided separately from the first gas meter based on the heating value of the gas of the first gas meter that is arranged within a predetermined range with respect to the second gas meter on a gas supply pipe configured to supply the gas.

Advantageous Effects of Invention

According to the present invention, it is possible to estimate the heating value of the gas with high accuracy in the gas meter capable of measuring only the flow rate of the gas.

DESCRIPTION OF EMBODIMENTS

Figure 1:
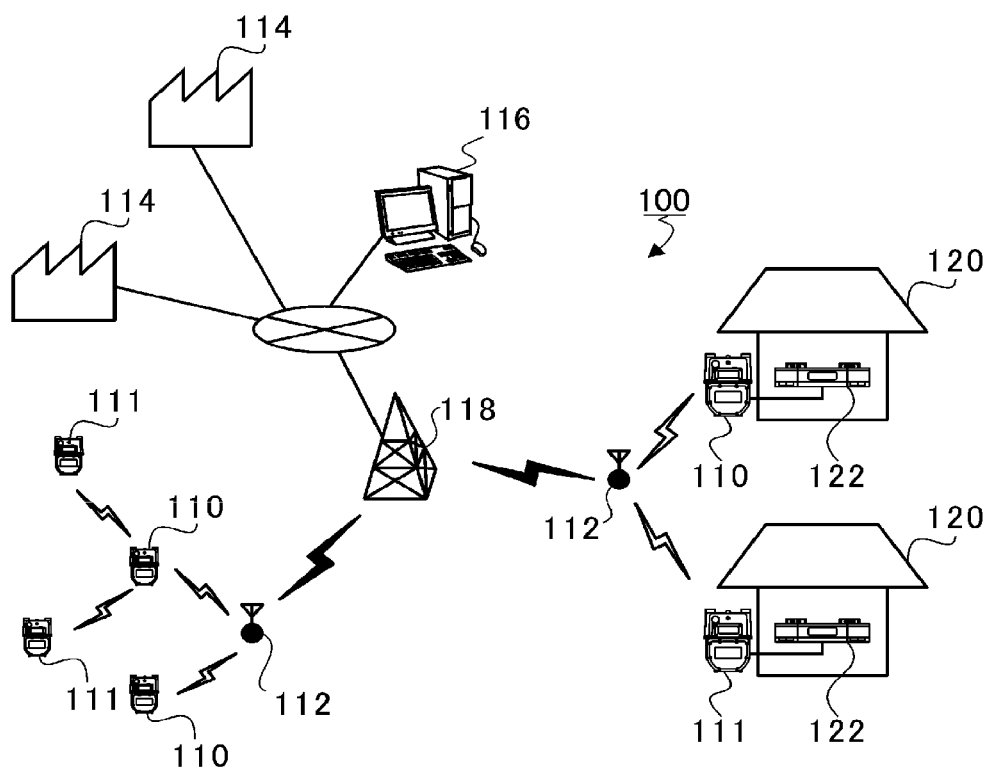
FIG. 1 is an explanatory diagram for illustrating a schematic configuration relating to information transmission of a gas meter system.

Now, with reference to the attached drawings, a preferred embodiment of the present invention is described in detail. The dimensions, materials, and other specific numerical values represented in the embodiment are merely examples used for facilitating the understanding of the invention, and do not limit the present invention otherwise particularly noted. Elements having substantially the same functions and configurations herein and in the drawings are denoted by the same reference symbols to omit redundant description thereof. Further, illustration of elements with no direct relationship to the present invention is omitted.

(Gas Meter System 100)

FIG. 1 is an explanatory diagram for illustrating a schematic configuration relating to information transmission of a gas meter system 100. As illustrated in FIG. 1, the gas meter system 100 includes a plurality of first gas meters 110, a plurality of second gas meters 111 provided separately from the first gas meters 110, a plurality of gateway devices 112, a plurality of gas production plants 114, and a center device 116.

The first gas meter 110 is configured to derive a heating value per unit volume at a temperature during measurement of a gas supplied to a demand place 120 of the first gas meter 110 (hereinafter also called "unit heating value") and a passage heating value (gross heating value) of a gas that has passed through the first gas meter 110, and to control the gas that flows through a device 122 installed at the demand place 120 in accordance with an instruction from the center device 116 or the measured flow rate or heating value.

The second gas meter 111 is configured to derive a flow rate of the gas supplied to the demand place 120 of the second gas meter 111 and to control the gas that flows through the device 122 installed at the demand place 120 in accordance with an instruction from the center device 116 or the measured flow rate.

The gateway device 112 is configured to collect data of the first gas meters 110 and the second gas meters 111, and to distribute data to the first gas meters 110 and the second gas meters 111.

The gas production plant 114 is configured to produce a hydrocarbon gas to be supplied to the demand place.

The center device 116 is constructed by, for example, a computer, and belongs to an administrator side of the gas meter system 100, for example, a gas utility. The center device 116 is configured to collect data of one or a plurality of gateway devices 112, and to distribute data to one or a plurality of gateway devices 112. Therefore, the center device 116 can collectively manage the information of the first gas meters 110 and the second gas meters 111 arranged at any demand places 120.

In this case, between the gateway device 112 and the center device 116, wireless communication is executed through, for example, existing communication networks such as a mobile phone network and a personal handy-phone system (PHS) network including a base station 118. Further, between the first gas meter 110 and the first gas meter 110, between the second gas meter 111 and the second gas meter 111, and between the first gas meter 110, the second gas meter 111, and the gateway device 112, wireless communication is executed through, for example, a smart meter wireless system (U-Bus Air) using a 920 MHz band.

Further, the center device 116 executes wired communication to/from the gas production plant 114 through the existing communication network to collect information of one or a plurality of gas production plants 114.

Figure 2:
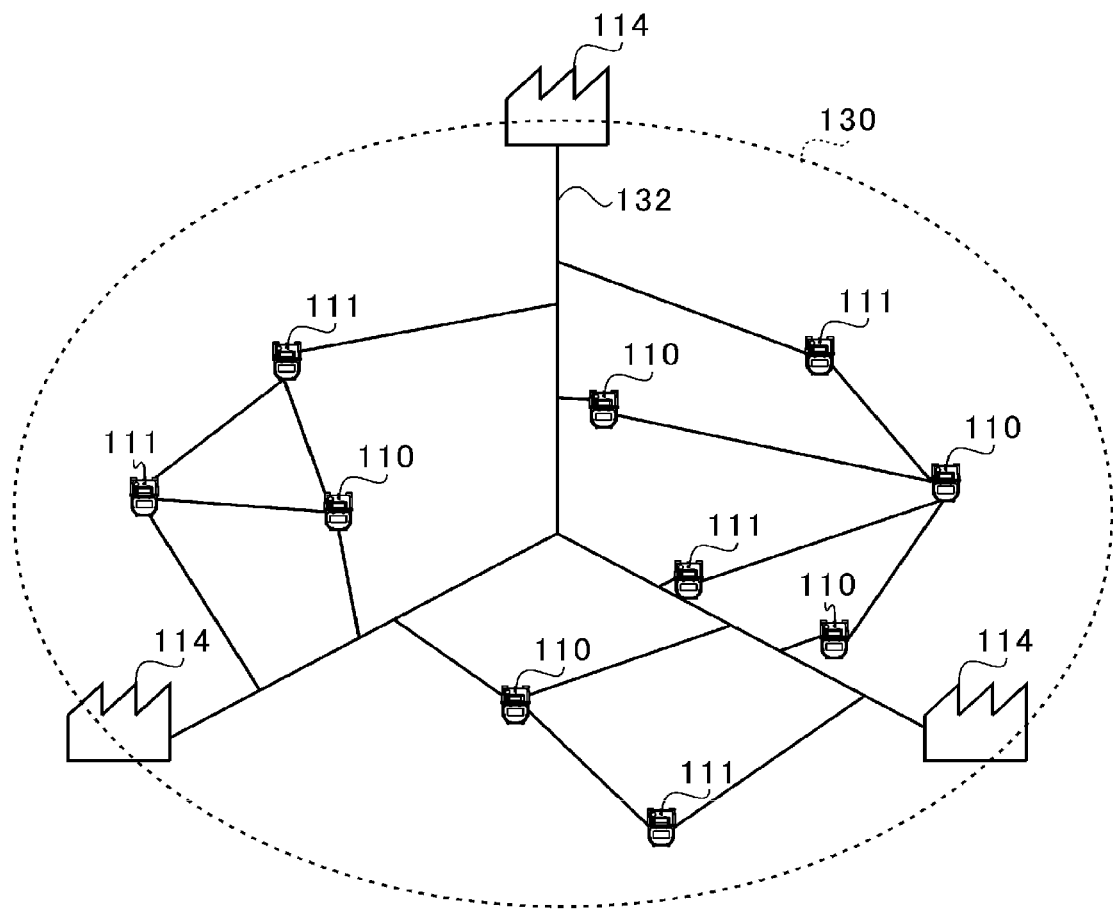
FIG. 2 is a diagram for illustrating a gas supply pipeline network.

FIG. 2 is a diagram for illustrating a gas supply pipeline network 130. As illustrated in FIG. 2, the gas supply pipeline network 130 includes gas supply pipes 132 spread out to the plurality of first gas meters 110, the plurality of second gas meters 111, and the plurality of gas production plants 114. In other words, the plurality of first gas meters 110, the plurality of second gas meters 111, and the plurality of gas production plants 114 are connected to one another via the gas supply pipeline network 130 (gas supply pipes 132).

The gases produced in the plurality of gas production plants 114 are supplied to the first gas meters 110 and the second gas meters 111 through the gas supply pipes 132 forming the gas supply pipeline network 130. Therefore, the gas supply pipeline network 130 is supplied with the gases produced in the plurality of gas production plants 114. The movement of the gas due to gas transportation in the gas pipes is overwhelmingly faster than the diffusion of the gas in the gas pipes, and hence there is little mixture of the gases produced in the plurality of gas production plants 114.

Meanwhile, each of the first gas meter 110 and the second gas meter 111 is supplied with, among the gases produced in the plurality of gas production plants 114, a gas produced in any one gas production plant 114. Further, even in the same first gas meter 110 or second gas meter 111, depending on time, a producer (gas production plant 114) of the gas to be supplied may vary, that is, the gas to be supplied may vary.

As described above, in the gas meter system 100, for example, in a transition period in which the second gas meter 111 is replaced with the first gas meter 110, there is a period in which the second gas meter 111 configured to derive only the flow rate of the gas and the first gas meter 110 capable of deriving the unit heating value are both installed. In such a transition period, inequality may occur between a customer charged based on the passage volume of the gas and a customer charged based on the unit heating value and the flow rate, that is, the passage heating value.

In view of this, in the gas meter system 100 of the present invention, the passage heating value of the second gas meter 111 is estimated based on the fact that the unit heating value of the second gas meter 111 is equal to the unit heating value derived by the first gas meter 110 installed within a predetermined range in the gas supply pipeline network 130 with respect to the second gas meter 111. With this, the unit heating value of the gas in the second gas meter 111 capable of deriving only the passage volume of the gas can be obtained with high accuracy. Now, details of the first gas meter 110, the second gas meter 111, and the center device 116 are described.

(First Gas Meter 110)

Figure 3:
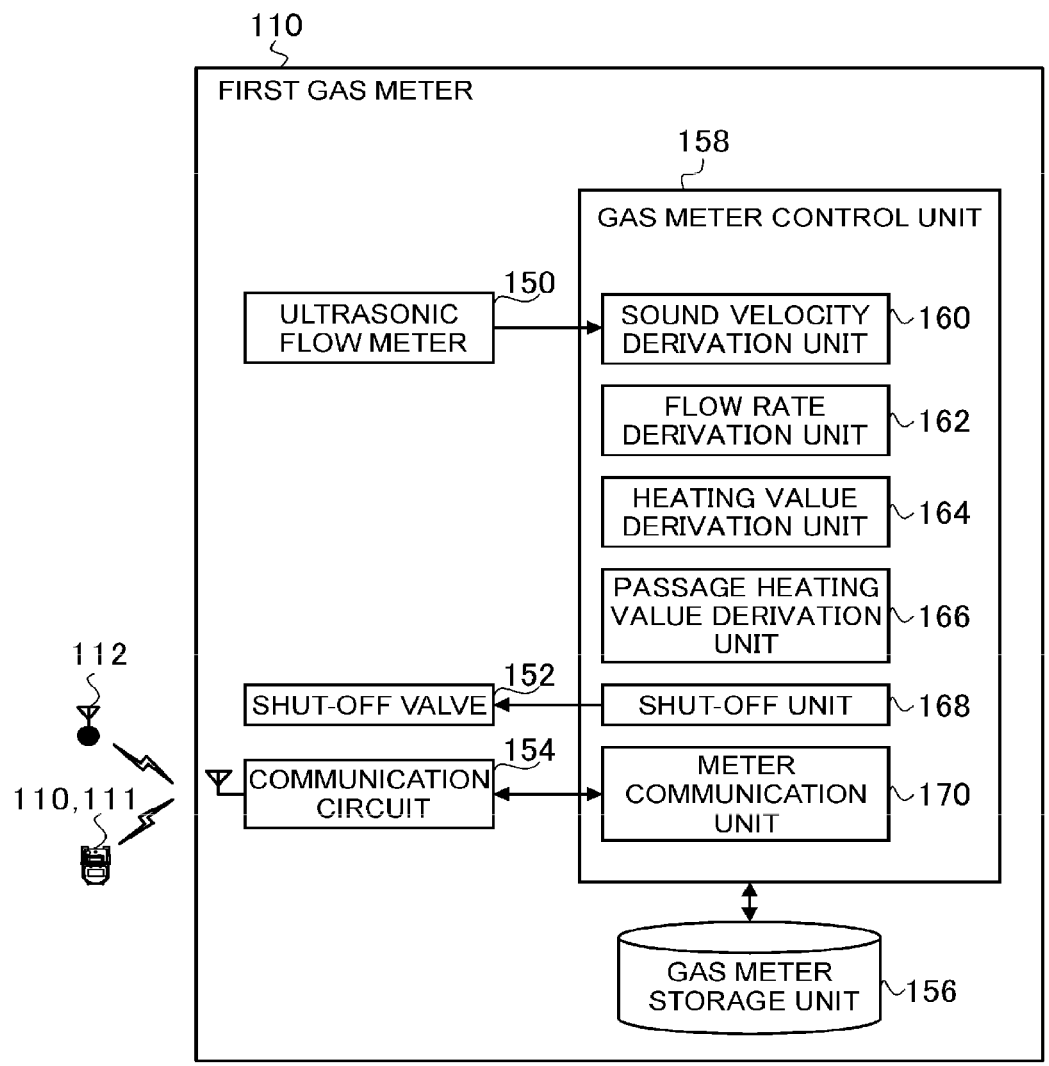
FIG. 3 is a functional block diagram for illustrating a schematic configuration of a first gas meter.

FIG. 3 is a functional block diagram for illustrating a schematic configuration of the first gas meter 110. The first gas meter 110 includes an ultrasonic flow meter 150, a shut-off valve 152, a communication circuit 154, a gas meter storage unit 156, and a gas meter control unit 158.

Figure 4:
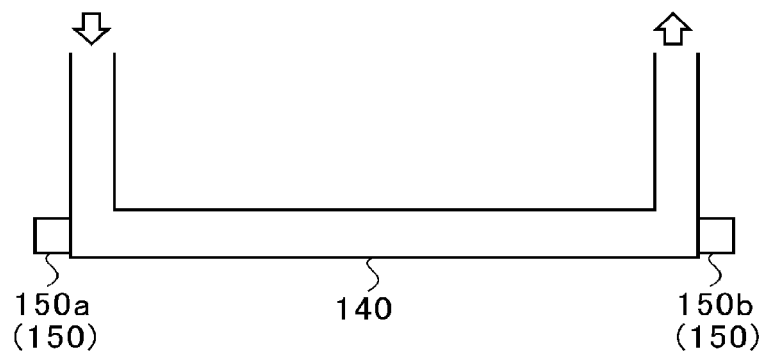
FIG. 4 is a diagram for illustrating a configuration of an ultrasonic flow meter.

FIG. 4 is a diagram for illustrating a configuration of the ultrasonic flow meter 150. The ultrasonic flow meter 150 is a flow meter using an arrival time difference, and, as illustrated in FIG. 4, includes a pair of ultrasonic transducers 150a and 150b arranged at two locations on the upstream and the downstream along the flow of the gas flowing through a gas flow path 140 (indicated by the outline arrows in FIG. 4). The ultrasonic flow meter 150 can bi-directionally measure, for each unit time period, a propagation time period in which an ultrasonic wave propagates in the gas from one ultrasonic transducer 150a or 150b to the other ultrasonic transducer 150b or 150a. Propagation time periods t1 and t2 are used in a sound velocity derivation unit 160 to be described later.

In this case, the pair of ultrasonic transducers 150a and 150b is arranged on either of the upstream side and the downstream side of the gas flow path 140, and hence the ultrasonic wave propagating therebetween is affected by a flow velocity of the gas. The ultrasonic wave propagating from the upstream side to the downstream side accelerates, and the ultrasonic wave propagating from the downstream side to the upstream side decelerates. In this case, the propagation time period of the ultrasonic wave propagating from the upstream ultrasonic transducer 150a to the downstream ultrasonic transducer 150b is represented by t1, and the propagation time period of the ultrasonic wave propagating from the downstream ultrasonic transducer 150b to the upstream ultrasonic transducer 150a is represented by t2.

Referring back to FIG. 3, the shut-off valve 152 is constructed by, for example, an electromagnetic valve using a solenoid or a stepping motor, and is configured to shut off or open the gas flow path 140. The communication circuit 154 is configured to establish wireless communication to/from the gateway device 112, other first gas meters 110, and the second gas meters 111. The gas meter storage unit 156 is constructed by, for example, a ROM, a RAM, a flash memory, or an HDD, and is configured to store programs and various types of data to be used in the first gas meter 110.

The gas meter control unit 158 is constructed by a CPU or a DSP, and is configured to use the programs stored in the gas meter storage unit 156 to control the entire first gas meter 110. Further, the gas meter control unit 158 functions as the sound velocity derivation unit 160, a flow rate derivation unit 162, a heating value derivation unit 164, a passage heating value derivation unit 166, a shut-off unit 168, and a meter communication unit 170.

The sound velocity derivation unit 160 is configured to derive the sound velocity based on the propagation time periods t1 and t2 measured by the ultrasonic flow meter 150. The flow rate derivation unit 162 is configured to derive the flow rate of the gas based on the propagation time periods t1 and t2 measured by the ultrasonic flow meter 150. The heating value derivation unit 164 is configured to derive the unit heating value (MJ/m$^3$) of the gas based on the sound velocity derived by the sound velocity derivation unit 160. In general, a gas expands at high temperature and contracts at low temperature. In the present invention, the heating value per unit volume at the temperature during measurement is derived.

The passage heating value derivation unit 166 is configured to derive the passage heating value of the gas that has passed through the first gas meter 110, that is, the gross heating value of the gas consumed at the demand place 120 provided with the first gas meter 110, based on the unit heating value of the gas derived by the heating value derivation unit 164 and on the flow rate detected by the flow rate derivation unit 162. The shut-off unit 168 is configured to control the shut-off valve 152 to control supply and demand of the gas. The meter communication unit 170 is configured to exchange information with the center device 116 via the communication circuit 154, to thereby transmit, for example, the unit heating value derived by the heating value derivation unit 164 and the passage heating value derived by the passage heating value derivation unit 166 to the center device 116 for each hour. This embodiment holds true even in a configuration without the shut-off unit 168 or the shut-off valve 152.

Now, detailed processing of the sound velocity derivation unit 160, the flow rate derivation unit 162, the heating value derivation unit 164, and the passage heating value derivation unit 166 is described.

(Sound Velocity Derivation Unit 160)

Figure 5:
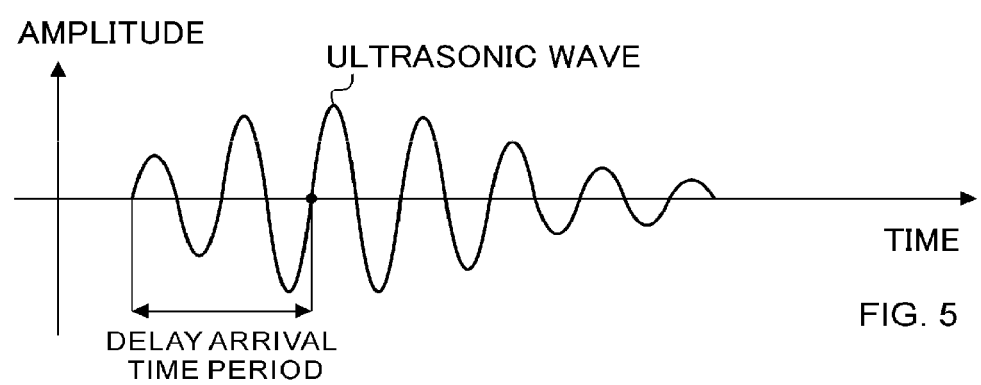
FIG. 5 is a diagram for illustrating a waveform of an ultrasonic wave received by an ultrasonic transducer of the ultrasonic flow meter.

FIG. 5 is a diagram for illustrating a waveform of an ultrasonic wave received by the ultrasonic transducer 150a or 150b of the ultrasonic flow meter 150. As illustrated in FIG. 5, the ultrasonic wave received by the ultrasonic transducer 150a or 150b of the ultrasonic flow meter 150 has a small amplitude immediately after start of the reception, and the amplitude is gradually increased to reach a peak after several waves. After that, the amplitude is decreased again. When the ultrasonic transducer 150a or 150b receives the ultrasonic wave transmitted from the paired ultrasonic transducer 150b or 150a, it is difficult for the ultrasonic transducer 150a or 150b to highly accurately define the arrival time period corresponding to the first several waves having a small amplitude due to the problems of sensitivity and an S/N ratio. Therefore, the ultrasonic transducer 150a or 150b determines that the ultrasonic wave is received when the ultrasonic wave that is increased to have a certain level of amplitude and detected after several waves crosses zero (indicated by the black dot in FIG. 5).

Therefore, in the ultrasonic flow meter 150, each of the propagation time periods t1 and t2 from the transmission to the reception of the ultrasonic wave is a time period that is longer than an arrival time period corresponding to an original time period by a delay arrival time period corresponding to about 2 wavelengths. That is, each of propagation time periods t1 and t2 has an error corresponding to the delay arrival time period.

In this case, as described in detail later, the gas flow rate derived by the flow rate derivation unit 162 is derived based on the difference between the propagation time period t1 and the propagation time period t2. Therefore, even when each of the propagation time periods t1 and t2 has an error corresponding to the delay arrival time period with respect to the arrival time period corresponding to the original arrival time period, the delay arrival time period can be cancelled by taking a difference between the propagation time period t1 and the propagation time period t2. Therefore, the derivation of the flow rate is less affected by the error.

Meanwhile, the sound velocity derivation unit 160 derives the sound velocity based on the propagation time periods t1 and t2 measured by the ultrasonic flow meter 150. Therefore, when there is an error corresponding to the delay arrival time period in each of the propagation time periods t1 and t2, the derivation of the sound velocity is affected by the error.

In view of this, the sound velocity derivation unit 160 subtracts the delay arrival time period being the error from each of the propagation time periods t1 and t2 measured by the ultrasonic flow meter 150 so as to derive arrival time periods ta1 and ta2 corresponding to the original arrival time periods, to thereby reduce the influence of the error as much as possible.

Then, the arrival time periods ta1 and ta2 corresponding to the original arrival time periods can be expressed by Expression (1).

$$ta1 = \frac{L}{C+V}, ta2 = \frac{L}{C-V} \quad (1)$$

In Expression (1), L represents a distance between the pair of ultrasonic transducers 150a and 150b, and V represents a flow velocity of the gas.

Therefore, the sound velocity derivation unit 160 derives the sound velocity C based on the arrival time periods ta1 and ta2 corresponding to the original arrival time periods with use of Expression (2) obtained by combining the equations of Expression (1).

$$C = \frac{L}{2}\left(\frac{1}{ta1} + \frac{1}{ta2}\right) \quad (2)$$

As described above, the sound velocity derivation unit 160 subtracts the delay arrival time period of the ultrasonic wave having a small amplitude and thus incapable of being detected from each of the propagation time periods t1 and t2 measured by the ultrasonic flow meter 150, and derives the sound velocity C based on the arrival time periods ta1 and ta2 corresponding to the original arrival time periods with use of Expression (2) obtained by combining the equations of Expression (1). In this manner, the sound velocity C can be derived with high accuracy. The delay arrival time period may be measured in advance through experiment for each of the sound velocity derivation units 160, or, when the sound velocity derivation units 160 having the same design are used, a standard delay arrival time period may be measured to omit measurement of each sound velocity derivation unit 160. Further, the arrival time periods ta1 and ta2 corresponding to the arrival time periods may be corrected from the propagation time periods t1 and t2 based on the transmission time of the transmitted ultrasonic wave and the reception time of the received ultrasonic wave.

(Flow Rate Derivation Unit 162)

The flow rate derivation unit 162 derives the flow velocity V of the gas based on the propagation time periods t1 and t2 measured by the ultrasonic flow meter 150 with use of Expression (3).

$$V = \frac{L}{2}\left(\frac{1}{t1} - \frac{1}{t2}\right) \quad (3)$$

Then, the flow rate derivation unit 162 multiplies the derived flow velocity V of the gas by the cross-sectional area of the gas flow path 140, to thereby derive the flow rate of the gas.

(Heating Value Derivation Unit 164)

Figure 6:
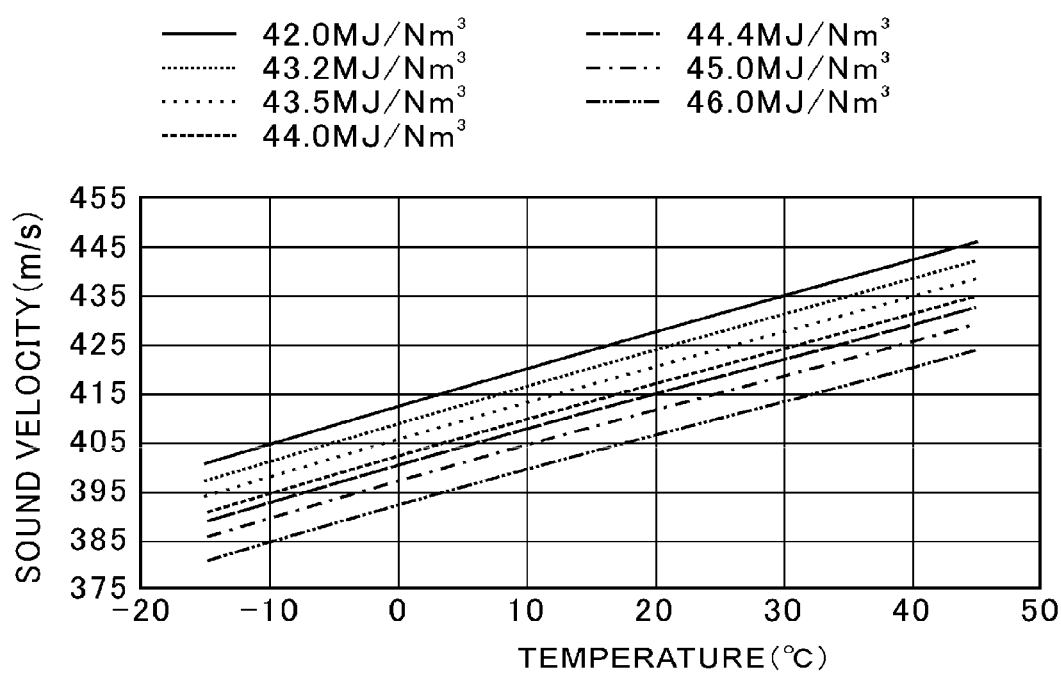
FIG. 6 is a graph for showing a relationship among temperature, a sound velocity, and a type (heating value in a standard state) of a gas.
Figure 7:
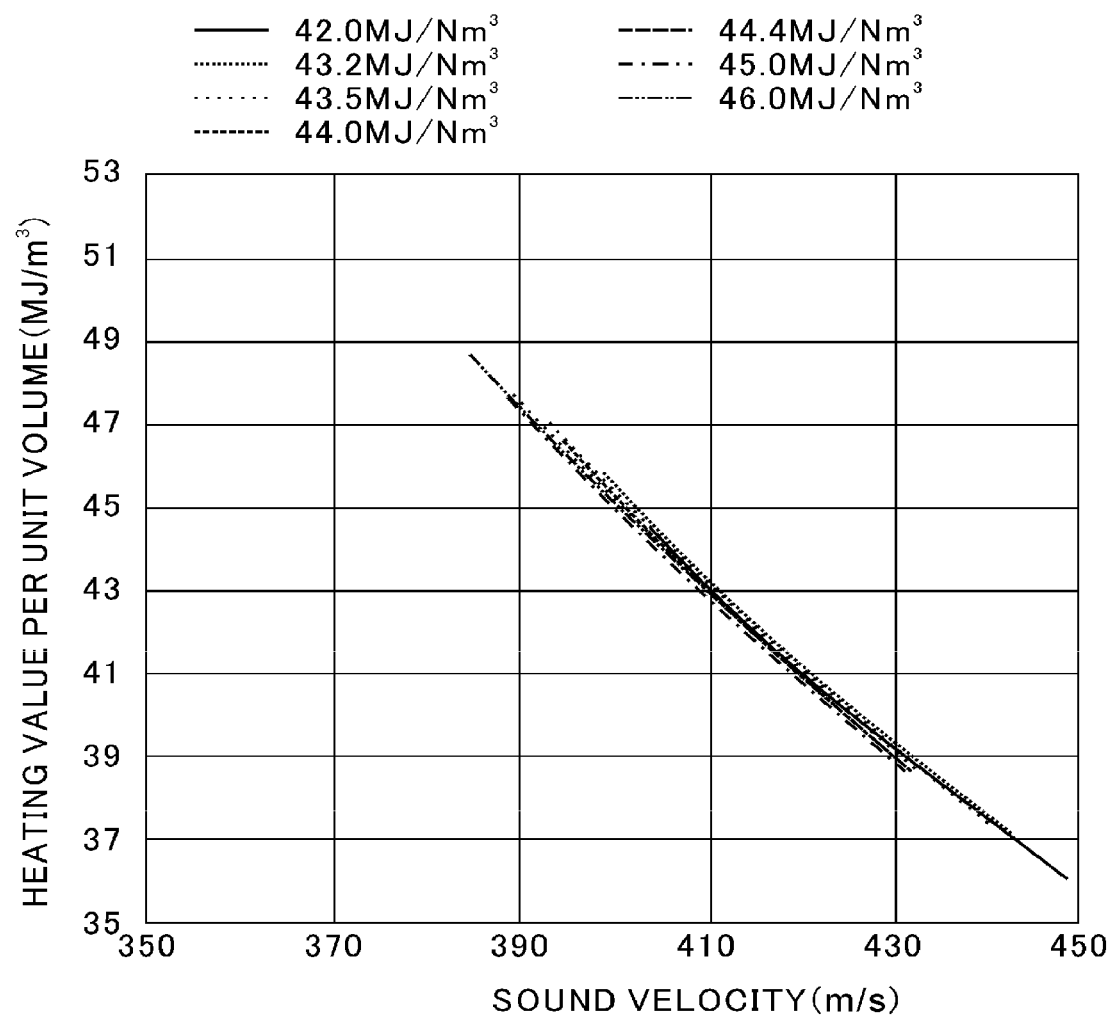
FIG. 7 is a graph for showing a relationship between the sound velocity and a unit heating value.

FIG. 6 is a graph for showing a relationship among temperature, a sound velocity, and a type (heating value in a standard state) of a gas. FIG. 7 is a graph for showing a relationship between the sound velocity and the unit heating value. In the following, the heating value in the standard state is also called "standard heating value".

As shown in FIG. 6, regardless of the type (standard heating value) of the gas, the sound velocity of the gas is decreased as the temperature of the gas is decreased, and the sound velocity of the gas is increased as the temperature of the gas is increased. Meanwhile, when the type (standard heating value) of the gas differs, the sound velocity of the gas differs even at the same gas temperature, and the temperature of the gas differs even at the same gas sound velocity. In more detail, as the standard heating value of the gas is increased, the sound velocity of the gas is decreased even at the same gas temperature, and the temperature of the gas is increased even at the same gas sound velocity.

In accordance with such characteristics, the type (standard heating value) of the gas can be estimated when the temperature and the sound velocity of the gas can be identified. For example, when the temperature of the gas is 20° C. and the sound velocity of the gas is 415 m/s, the type (standard heating value) of the gas can be estimated to be 44.4 MJ/Nm$^3$.

In view of this, the related-art gas meter has measured the temperature and the sound velocity of the gas to estimate the standard heating value based on the measured temperature and sound velocity of the gas. However, the related-art gas meter requires a temperature sensor in order to measure the temperature of the gas in addition to the sound velocity of the gas, and hence there has been a problem in that not only the cost increases but also the configuration becomes complicated.

Now, based on the relationship among the temperature, the sound velocity, and the type (standard heating value) of the gas shown in FIG. 6, temperatures and unit heating values of different types (standard heating values) of gas in the case of the same sound velocity of 405 m/s are shown in Table 1.

TABLE 1

| Type of gas (MJ/Nm$^3$) | 42.0 | 43.2 | 43.5 | 44.0 | 44.4 | 45.0 | 46.0 |
|---|---|---|---|---|---|---|---|
| Temperature (° C.) | −8.3 | −4.5 | 0.5 | 4.5 | 7.0 | 12.0 | 19.0 |
| Unit heating value (MJ/m$^3$) | 43.3 | 43.9 | 43.4 | 43.3 | 43.3 | 43.1 | 43.0 |

As is apparent from Table 1 as well, in the case of the same sound velocity of 405 m/s, regardless of the type (standard heating value) of the gas and the temperature, the unit heating value is a constant value that falls within the range of about 43.5±0.5 MJ/m$^3$.

Further, as shown in FIG. 7, regardless of the type (standard heating value) of the gas, the sound velocity and the unit heating value can be represented in a substantially collinear relationship. Therefore, it can be understood that, regardless of the type (standard heating value) of the gas, the unit heating value can be derived based on only the sound velocity. In Table 1 and FIG. 7, there is a slight error in the relationship between the sound velocity and the unit heating value depending on the type (standard heating value) of the gas, but the error is within about ±2.5%. Thus, the unit heating value can be derived with high accuracy with use of only the sound velocity regardless of the type of the gas.

Now, how the unit heating value can be derived based on only the sound velocity is theoretically described.

The sound velocity C can be represented by Expression (4).

$$C = \sqrt{\frac{\gamma RT}{M}} \quad (4)$$

In Expression (4), γ represents a specific heat ratio of a gas mixture, R represents a gas constant (J/(mol·K)), and M represents an average molecular weight of a gas mixture (kg/mol).

Further, the relationship between a gas density (average molecular weight) and the standard heating value can be represented by Expression (5).

$$CV_0 = aM + b \quad (5)$$

In Expression (5), $CV_0$ represents a standard heating value (kJ/Nm³), and a and b are constants (in the case of an ideal gas of saturated hydrocarbon, $a=2.1\times10^6$ and $b=7.4\times10^3$, and in the case of an actual gas of saturated hydrocarbon, $a=2.4\times10^6$ and $b=5.7\times10^2$).

Further, the unit heating value of the gas at a temperature T can be represented by Expression (6).

$$CV_T = \frac{pT_0}{p_0 T} CV_0 \quad (6)$$

In Expression (6), $CV_T$ represents a unit heating value (kJ/m³) at the temperature T, p represents a pressure (supply pressure, Pa) at the temperature T, $p_0$ represents a standard pressure (101,325 Pa), and $T_0$ represents a standard temperature (273.15 K).

Expression (7) can be derived based on Expression (4) to Expression (6).

$$CV_T = \frac{1}{C^2} \frac{\gamma RT_0 p}{p_0} \left(a + \frac{b}{M}\right) \quad (7)$$

In Expression (7), M is from about 16 to about 20 in the case of a city gas, and thus the relationship of a>>b/M is satisfied. Therefore, Expression (7) can be represented as Expression (8).

$$CV_T = \frac{1}{C^2} \frac{a\gamma RT_0 p}{p_0} \quad (8)$$

As described above, Expression (8) is not affected by the temperature T during measurement. Therefore, it is understood that, when the supply pressure p is known, the unit heating value can be derived based on only the sound velocity C without measuring the temperature T. When the unit heating value is derived based on only the sound velocity C without measuring the temperature T, the unit heating value can be derived with higher accuracy to some extent in a case where the gas is a straight-chain saturated hydrocarbon gas. Further, it is known that the sound velocity is hardly affected by pressure, and hence the pressure p may be corrected as necessary based on the general Boyle's law by measuring the pressure.

In view of this, the heating value derivation unit 164 refers to correspondence relationship information that enables the unit heating value to be uniquely derived in advance from the sound velocity of the gas, to thereby derive the unit heating value (MJ/m³) of the gas based on the sound velocity derived by the sound velocity derivation unit 160. As long as the unit heating value can be uniquely derived from the sound velocity of the gas, the correspondence relationship information may be, for example, an expression that enables the unit heating value to be derived from the sound velocity or a table that enables the unit heating value to be derived from the sound velocity.

(Passage Heating Value Derivation Unit 166)

The passage heating value derivation unit 166 integrates a product of the unit heating value of the gas derived by the heating value derivation unit 164 and the flow rate derived by the flow rate derivation unit 162 with respect to the time axis, to thereby derive the passage heating value of the gas. In this case, the passage heating value derivation unit 166 of the first gas meter 110 derives the passage heating value, but the center device 116 may derive the passage heating value in order to ensure the equality in derivation of the passage heating value with the second gas meter 111 regarding the frequency of deriving the passage heating value. The unit heating value and the passage heating value that are derived as described above are transmitted to the center device 116 for each hour.

With this, the first gas meter 110 is capable of deriving the unit heating value by measuring only the sound velocity regardless of the type (standard heating value) of the hydrocarbon gas. At this time, the first gas meter 110 uses correspondence relationship information to correct the expansion/contraction of the gas due to the temperature of the gas without measuring the temperature. With this, as compared to the related-art gas meter, the passage heating value of the gas can be derived with lower cost and a simpler configuration. Further, the gas utility can appropriately charge the fees based on the passage heating value.

(Second Gas Meter 111)

Figure 8:
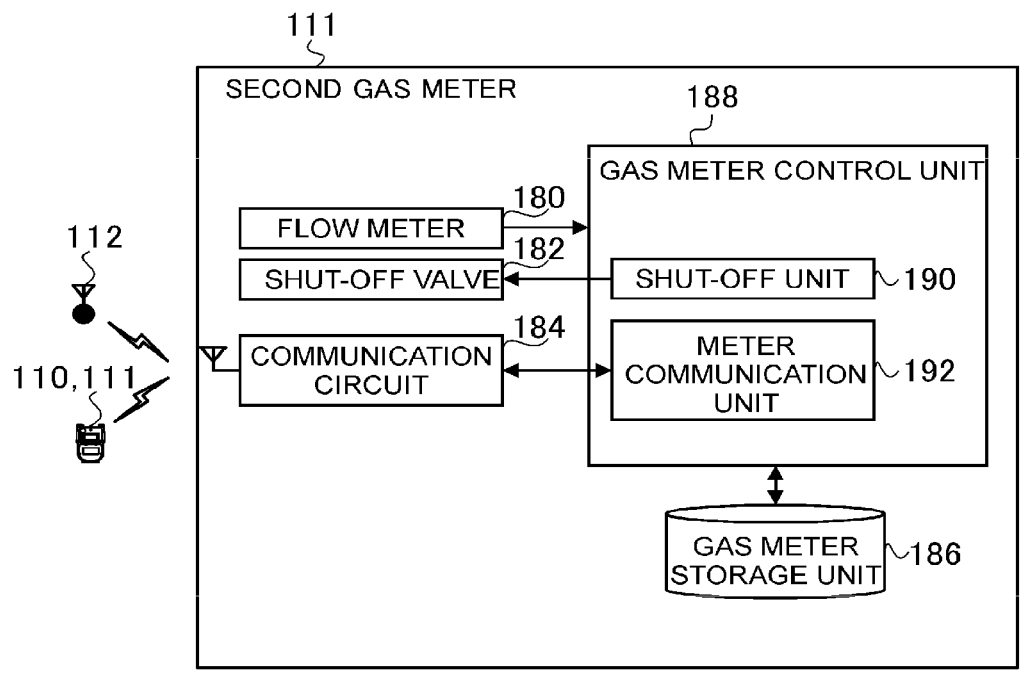
FIG. 8 is a functional block diagram for illustrating a schematic configuration of a second gas meter.

FIG. 8 is a functional block diagram for illustrating a schematic configuration of the second gas meter 111. As illustrated in FIG. 8, the second gas meter 111 includes a flow meter 180, a shut-off valve 182, a communication circuit 184, a gas meter storage unit 186, and a gas meter control unit 188. Unlike the first gas meter 110, the second gas meter 111 cannot derive the sound velocity and the unit heating value of the gas.

The flow meter 180 is configured to measure the flow-rate value of the gas passing through the second gas meter 111. The shut-off valve 182 is constructed by, for example, an electromagnetic valve using a solenoid or a stepping motor, and is configured to shut off or open a flow path of the gas. The communication circuit 184 is configured to establish wireless communication to/from the gateway device 112, the first gas meters 110, and other second gas meters 111. The gas meter storage unit 186 is constructed by, for example, a ROM, a RAM, a flash memory, or an HDD, and is configured to store programs and various types of data to be used in the second gas meter 111.

The gas meter control unit 188 is constructed by a CPU or a DSP, and is configured to use the programs stored in the gas meter storage unit 186 to control the entire second gas meter 111. Further, the gas meter control unit 188 functions as a shut-off unit 190 and a meter communication unit 192.

The shut-off unit 190 is configured to control the shut-off valve 182 to control supply and demand of the gas. The meter communication unit 192 is configured to exchange information with the center device 116 via the communication circuit 184, to thereby transmit, for example, the information on the flow rate measured by the flow meter 180 to the center device 116 for each hour. This embodiment holds true even in a configuration without the shut-off unit 190 or the shut-off valve 182.

(Center Device 116)

Figure 9:
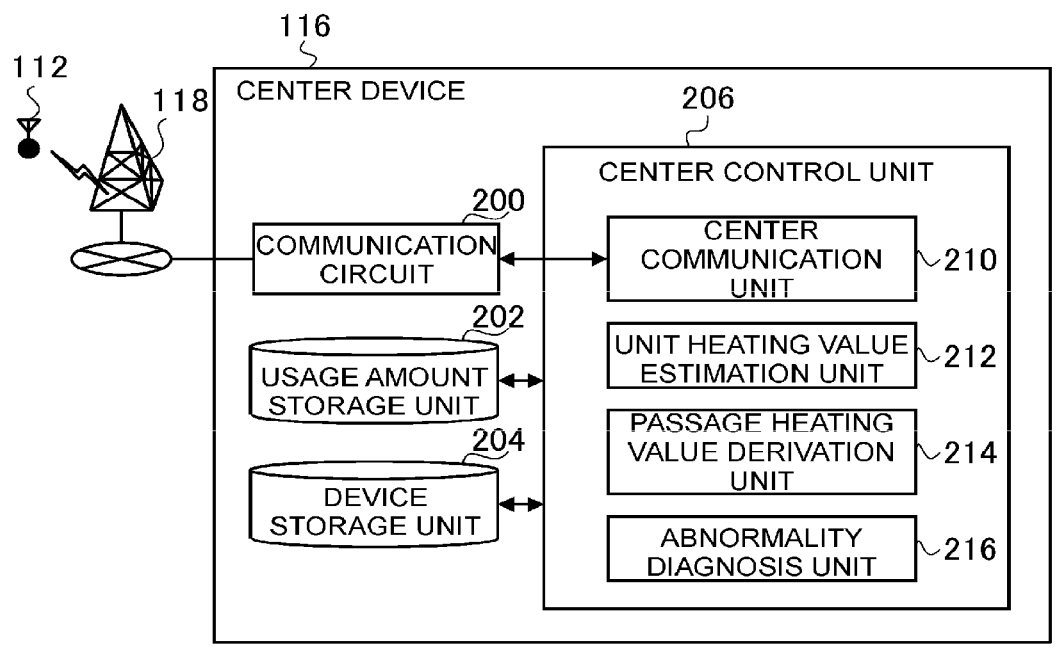
FIG. 9 is a functional block diagram for illustrating a schematic configuration of a center device.

FIG. 9 is a functional block diagram for illustrating a schematic configuration of the center device 116. As illustrated in FIG. 9, the center device 116 includes a communication circuit 200, a usage amount storage unit 202, a device storage unit 204, and a center control unit 206. The communication circuit 200 is configured to establish wireless communication to/from the gateway device 112 via the base station 118. The usage amount storage unit 202 is constructed by, for example, a ROM, a RAM, a flash memory, or an HDD, and is configured to store the unit heating value and the passage heating value received from each first gas meter 110 in association with the corresponding first gas meter 110. Therefore, the usage amount storage unit 202 stores the transition of the unit heating value and the passage heating value in the past for each first gas meter 110. Further, the usage amount storage unit 202 stores the flow rate received from each second gas meter 111 in association with the corresponding second gas meter 111. Therefore, the usage amount storage unit 202 stores the transition of the passage volume in the past for each second gas meter 111. Similarly to the usage amount storage unit 202, the device storage unit 204 is constructed by, for example, a ROM, a RAM, a flash memory, or an HDD, and is configured to store the device 122 to be used via the first gas meter 110 and the second gas meter 111, for example, a pilot flame device, in association with the corresponding first gas meter 110 and second gas meter 111.

The center control unit 206 is constructed by a CPU or a DSP, and is configured to control the entire center device 116 based on the information stored in the usage amount storage unit 202 or the device storage unit 204. Further, the center control unit 206 functions as a center communication unit 210, a unit heating value estimation unit 212, a passage heating value derivation unit 214, and an abnormality diagnosis unit 216.

The center communication unit 210 is configured to exchange information with each first gas meter 110 via the communication circuit 200, to thereby, for example, receive the unit heating value and the passage heating value of the gas from the first gas meter 110. Further, the center communication unit 210 is configured to exchange information with each second gas meter 111 via the communication circuit 200, to thereby, for example, receive the flow rate of the gas from the second gas meter 111.

The unit heating value estimation unit 212 is configured to estimate the unit heating value of the gas in the second gas meter 111. In this case, the usage amount storage unit 202 stores a supply pipeline network map representing the gas supply pipeline network 130 (gas supply pipes 132) in which the first gas meters 110, the second gas meters 111, and the gas production plants 114 are connected to one another as illustrated in FIG. 2.

The unit heating value estimation unit 212 refers to the supply pipeline network map to identify the first gas meter 110 that is arranged closest to the second gas meter 111 on the gas supply pipes 132. Then, the unit heating value estimation unit 212 estimates the unit heating value of the second gas meter 111 based on the unit heating value of the first gas meter 110 that is arranged closest on the gas supply pipes 132. Specifically, the unit heating value estimation unit 212 estimates that the unit heating value of the second gas meter 111 is the same as the unit heating value of the first gas meter 110 arranged closest on the gas supply pipes 132. The term "close" herein refers to not close in terms of a physical space but close along the pipeline routes on the pipeline network. The reason is because, even if two gas meters are installed in adjacent buildings, when gases are supplied to the two gas meters through different pipeline routes, the heating values of the gases supplied to the respective gas meters may not be regarded as the same.

Figure 10A:
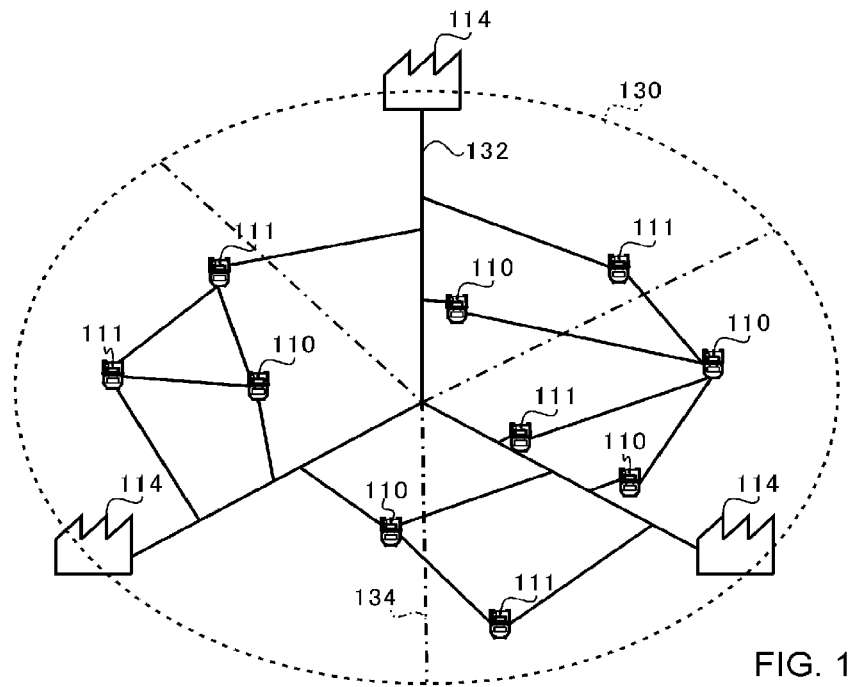
FIG. 10($a$) and FIG. 10($b$) are diagrams for illustrating a range in which gases produced in gas production plants are supplied in the gas supply pipeline network.
Figure 10B:
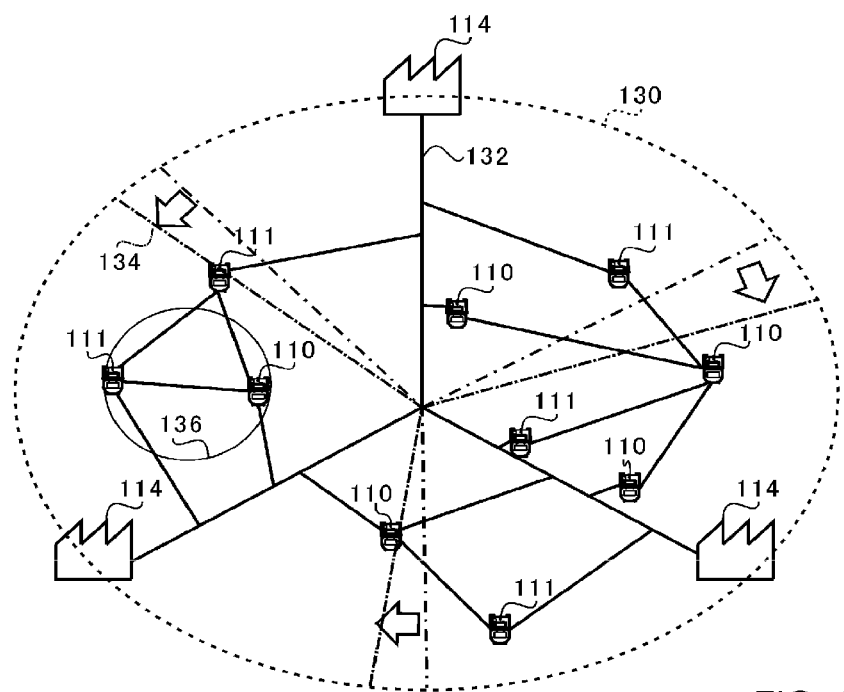

FIG. 10(a) and FIG. 10(b) are diagrams for illustrating a range in which gases produced in the gas production plants 114 are supplied in the gas supply pipeline network 130. In this case, the second gas meter 111 is highly likely to be supplied with a gas produced in the same gas production plant 114 as that of the first gas meter 110 that is arranged closest on the gas supply pipes 132.

For example, as illustrated in FIG. 10(a), it is assumed that, in the gas supply pipeline network 130, boundaries 134 serve as borders for supplying the gases produced in the respective gas production plants 114 to the first gas meters 110 and the second gas meters 111. Then, as illustrated in FIG. 10(b), in the gas supply pipeline network 130, as the supply range of the gas produced in each gas production plant 114 changes as time elapses, the boundaries 134 change as well.

Even when the boundaries 134 change as described above, the unit heating value of the second gas meter 111 is estimated based on the unit heating value of the first gas meter 110 that is arranged closest on the gas supply pipes 132. Thus, the unit heating value of the second gas meter 111 can be estimated with high accuracy.

The passage heating value derivation unit 214 is configured to integrate a product of the passage volume of the gas received from the second gas meter 111 and the unit heating value of the gas estimated by the unit heating value estimation unit 212 with respect to the time axis, to thereby derive the passage heating value of the gas of the second gas meter 111.

The abnormality diagnosis unit 216 is configured to diagnose whether or not the present passage heating value is abnormal based on the transition of the passage heating value in the past, which is stored in the usage amount storage unit 202. Further, the abnormality diagnosis unit 216 can diagnose the abnormality also based on the rating passage heating value of the gas in the device 122, which is stored in the device storage unit 204.

As described above, in the gas meter system 100 (heating value estimation method) in which the first gas meter 110 capable of deriving the unit heating value and the second gas meter 111 capable of deriving the passage volume are connected to each other via the gas supply pipeline network 130, the unit heating value of the second gas meter 111 is estimated based on the unit heating value of the first gas meter 110 that is arranged closest on the gas supply pipes 132. With this, for example, even in the transition period in which the second gas meter 111 is replaced with the first gas meter 110, the unit heating value of the second gas meter 111 can be estimated with high accuracy. Further, the gas utility can appropriately charge the fees from the customer of the demand place 120 at which the second gas meter 111 is installed based on the estimated unit heating value of the gas.

Incidentally, in a specific area (gas supply pipeline network) in which gases are supplied from a plurality of inflow ports connected to a plurality of gas supply sources (gas production plant), a method of charging fees with use of an average heating value in the area, which is calculated based on the heating value and the flow rate that are measured at the plurality of inflow ports, is executed or planned. However, at a place close to the inflow port to which a gas having a lower heating value than the average heating value always flows, this method causes loss of the customer and gain of the gas utility when fees are charged based on the average heating value. In contrast, at a place close to the inflow port to which a gas having a higher heating value than the average heating value always flows, the method causes gain of the customer and loss of the gas utility when fees are charged based on the average heating value.

Further, when there are a pipeline service provider and a gas retailer in the gas utility, the following problems further arise with respect to the pipeline service provider and the gas retailer. A gas obtained by the gas retailer is supplied and sold to the customer via the pipeline of the pipeline service provider. At this time, deals are also made between the gas retailers and between the gas retailer and the pipeline service provider in addition to the conventional deal made between the gas company and the customer.

For example, it is assumed that one retailer obtains a gas having a lower heating value than an average value of the area to inject the gas to the specific area through one injection port, another retailer obtains a gas having a higher heating value than the average value of the area to inject the gas to the same area through another injection port, and customers each contracting with each of the gas retailers are scattered in the area. At this time, when the customers are averagely distributed in the area in which each gas for the customers reaches, only problems similar to the above-mentioned examples arise between the gas retailer and the customer. Meanwhile, when the distribution is biased, for example, a large number of customers contracting with the another retailer exist close to the injection port of the one retailer, and conversely a large number of customers contracting with the one retailer exist close to the injection port of the another retailer, although the one retailer supplies a lower heating value than the another retailer, for example, the one retailer may gain under a condition in which a gas of a passage volume at the average heating value is only required to be supplied to the area. As a result, the average heating value and the heating value of the gas that is actually used may be different from each other, and thus the inequality is not solved. As another method of eliminating inequality between the retailers, there may be a method of supplying a gas with use of a dedicated pipeline to the customer contracting with the one retailer, but this method is unrealistic because a different pipeline is installed every time a retailer is added.

In view of this, in the gas meter system 100, the unit heating value of the second gas meter 111 is estimated based on the unit heating value of the first gas meter 110 that is arranged closest on the gas supply pipes 132. Thus, the above-mentioned problems can be solved.

Modification Example

Figure 11:
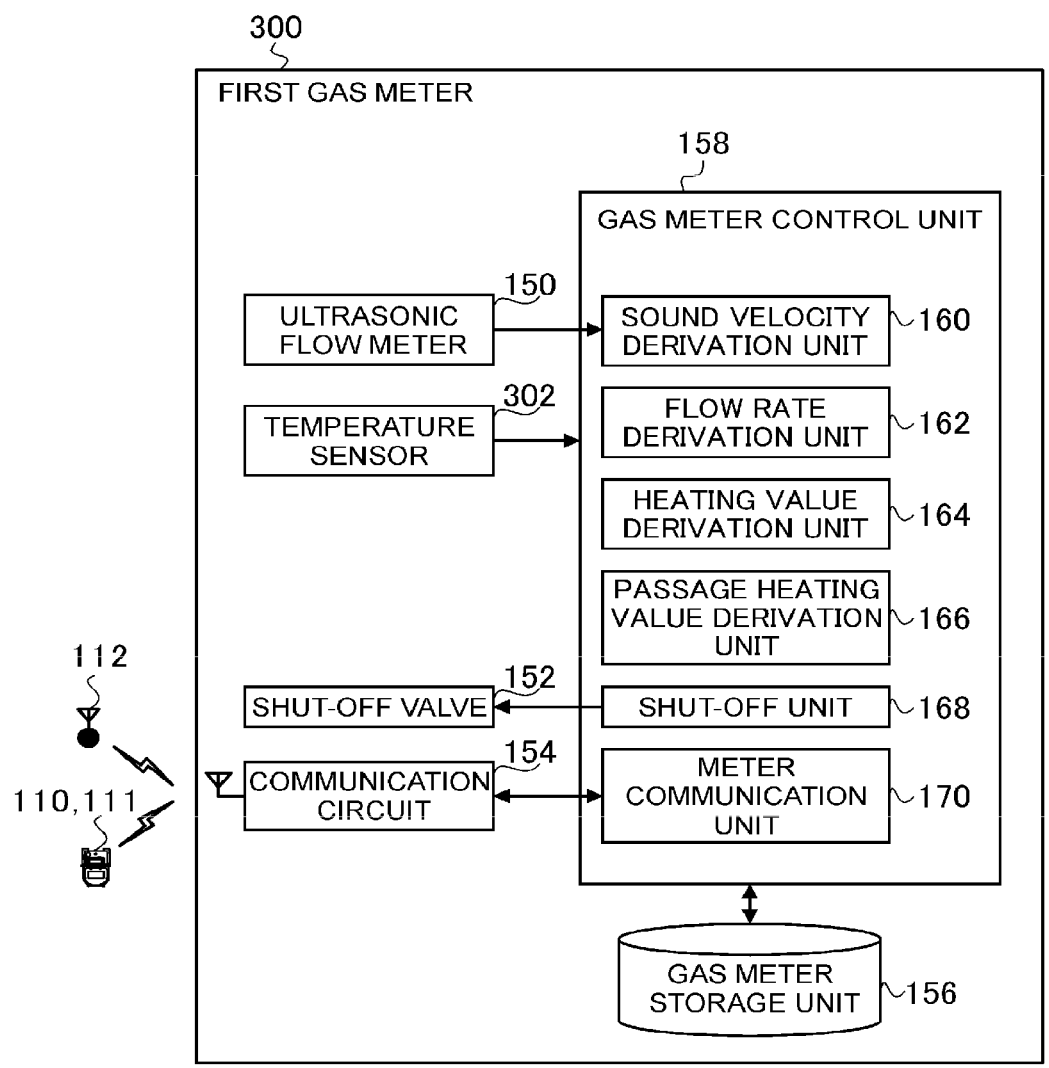
FIG. 11 is a functional block diagram for illustrating a schematic configuration of a first gas meter according to a modification example of the present invention.

FIG. 11 is a functional block diagram for illustrating a schematic configuration of a first gas meter 300 according to a modification example of the present invention. As illustrated in FIG. 11, the first gas meter 300 differs from the above-mentioned first gas meter 110 in that a temperature sensor 302 is provided. The remaining configuration is the same as that of the first gas meter 110.

The temperature sensor 302 measures the temperature of the supplied gas. Then, the heating value derivation unit 164 derives the unit heating value based on the sound velocity derived by the sound velocity derivation unit 160 and on the temperature measured by the temperature sensor 302. With this, the heating value derivation unit 164 can derive the unit heating value of the gas with higher accuracy than that of the first gas meter 110.

As described above, the first gas meter 300 can derive or measure the temperature and the sound velocity of the gas to derive the unit heating value of the gas based on the temperature and the sound velocity of the gas. With this, the derivation accuracy of the unit heating value of the gas can be improved.

The preferred embodiment of the present invention has been described above with reference to the attached drawings, but, needless to say, the present invention is not limited to the embodiment. It is apparent that those skilled in the art may arrive at various alternations and modifications within the scope of claims, and those examples are construed as naturally falling within the technical scope of the present invention.

In the above-mentioned embodiment, the first gas meter 110 includes the heating value derivation unit 164 and the passage heating value derivation unit 166, but the center device 116 may include those units. In this case, the first gas meter 110 may transmit the information of the sound velocity derived by the sound velocity derivation unit 160 to the center device 116.

Further, in the above-mentioned embodiment, the first gas meter 110 includes the communication circuit 154, but the first gas meter 110 may not include the communication circuit 154. In this case, the unit heating value, the passage heating value, or the flow rate of the gas that has passed through the first gas meter 110 is read by a meter reader for each month, for example. The read unit heating value, passage heating value, or flow rate of the gas may be stored in the center device 116.

Further, in the above-mentioned embodiment, the second gas meter 111 includes the communication circuit 184, but the second gas meter 111 may not include the communication circuit 184. In this case, the flow rate of the gas that has passed through the second gas meter 111 is read by a meter reader for each month, for example. The read flow rate of the gas is stored in the center device 116. Then, the center device 116 may derive the passage heating value based on the product of the monthly average value of the unit heating value of the first gas meter 110 that is arranged closest to the second gas meter 111 and the read flow rate of the gas.

Further, in the above-mentioned embodiment, the second gas meter 111 includes the communication circuit 184, but the second gas meter 111 may not include the communication circuit 184. In this case, the flow rate of the gas that has passed through the second gas meter 111 is read by a meter reader for each month, for example. The read flow rate of the gas is stored in the center device 116. Then, the center device 116 may estimate the monthly average unit heating value of the second gas meter 111 based on the monthly average unit heating value of the first gas meter 110 that is arranged closest to the second gas meter 111, and derive the passage heating value based on the product of the estimated monthly average unit heating value and the read flow rate of the gas.

Further, for example, the unit heating value of the second gas meter 111 may be estimated based on the unit heating value of the first gas meter 110 that is arranged closest among the first gas meters 110 through which a gas is passing during a time period that is the same as the time at which the gas passes through the second gas meter 111. That is, when the first gas meter 110 is not used, even the first gas meter 110 that is arranged closest to the second gas meter 111 may be excluded, and the closest first gas meter 110 may be identified from the first gas meters 110 used during the above-mentioned time period, to thereby estimate the unit heating value of the second gas meter 111 based on the unit heating value of the identified first gas meter 110.

Further, in the above-mentioned embodiment, the unit heating value of the second gas meter 111 is estimated based on the unit heating value of the first gas meter 110 that is arranged closest, but the unit heating value of the second gas meter 111 may be estimated based on the unit heating value of the first gas meter 110 that falls within a predetermined range 136 (FIG. 10(b)) on the gas supply pipes 132 with respect to the second gas meter 111.

Further, the first gas meter 300 may derive the heating value in the standard state based on the sound velocity derived by the sound velocity derivation unit 160 and on the temperature measured by the temperature sensor 302 to transmit the derived heating value to the center device 116, and the second gas meter 111 may include a temperature sensor to transmit the temperature measured by the temperature sensor in addition to the passage volume to the center device 116. The center device 116 may derive the unit heating value of the second gas meter 111 based on the heating value in the standard state derived by the first gas meter 300 and on the temperature and the passage volume that are measured or derived by the second gas meter 111.

Further, each of the first gas meter 110 and the second gas meter 111 may include a pressure sensor configured to measure a pressure of the supplied gas. In this case, the first gas meter 110 may correct the unit heating value based on the pressure measured by the pressure sensor (Expression (8)), and the second gas meter 111 may correct a volumetric flow rate based on the pressure measured by the pressure sensor. Further, the first gas meter 110 may include a pressure sensor configured to measure a pressure of the supplied gas, and the volumetric flow rate of the second gas meter 111 may be corrected based on the pressure measured by the first gas meter 110 close to the second gas meter 111.

Further, the gas production plant 114 may include gas chromatograph and desirably a sound velocity derivation unit as well. The gas production plant 114 may analyze the component of the produced gas by gas chromatograph to transmit results to the center device 116 as gas characteristics, and may transmit the sound velocity of the gas derived by the sound velocity derivation unit to the center device 116. Then, the center device 116 may identify the producer of the gas supplied to the first gas meter 110, that is, among the plurality of gas production plants 114, the gas production plant 114 producing the supplied gas based on the sound velocity itself or the time-series change of the sound velocity of the gas, which is received from the first gas meter 110, and on the gas characteristic and the sound velocity that are received from the gas production plant 114.

INDUSTRIAL APPLICABILITY

The present invention can be applied to a gas meter system and a heating value estimation method for deriving a unit heating value.

REFERENCE SIGNS LIST 100 gas meter system
110 first gas meter
111 second gas meter
114 gas production plant
116 center device
150 ultrasonic flow meter
160 sound velocity derivation unit
162 flow rate derivation unit
164 heating value derivation unit
166 passage heating value derivation unit (heating value derivation unit)
212 unit heating value estimation unit
214 passage heating value derivation unit

The invention claimed is:

1. A gas meter system, comprising:
first processing circuitry included in a first gas meter of a plurality of first gas meters, the first processing circuitry configured to derive a first heating value of a gas passing through the first gas meter; and
second processing circuitry configured to estimate a second heating value of a gas passing through a second gas meter provided separately from the first gas meter based on the first heating value of the gas of the first gas meter that is arranged within a predetermined range with respect to the second gas meter on a gas supply pipe configured to supply the gas,
wherein the first gas meter is a closest gas meter to the second gas meter among the plurality of first gas meters at which the gas passing through the first gas meter is at the same time as the gas passing through the second gas meter.

2. The gas meter system according to claim 1, wherein the first processing circuitry is further configured to derive a sound velocity of the gas supplied to the first gas meter,
wherein the first processing circuitry is further configured to derive the first heating value of the gas passing through the first gas meter based on the sound velocity of the gas derived by the first processing circuitry.

3. The gas meter system according to claim 2, further comprising a temperature sensor configured to measure a temperature of the gas supplied to the first gas meter,
wherein the first processing circuitry is further configured to derive the first heating value of the gas passing through the first gas meter based (i) on the sound velocity of the gas derived by the first processing circuitry, and (ii) on the temperature of the gas derived by the temperature sensor.

4. The gas meter system according to claim 3, wherein the second processing circuitry is further configured to diagnose whether a present heating value is abnormal based on a transition of the first heating value derived by the first processing circuitry.

5. The gas meter system according to claim 3, further comprising:
a center apparatus that is in communication with the first gas meter and the second gas meter,
wherein the first gas meter is further configured to transmit the first heat value to the center apparatus,
wherein the second gas meter includes a temperature sensor configured to measure a temperature of the gas passing through the second gas meter, and
wherein the measured temperature of the gas passing through the second gas meter is transmitted to the center apparatus.

6. The gas meter system according to claim 2, wherein the gas comprises a hydrocarbon gas.

7. The gas meter system according to claim 6, further comprising a temperature sensor configured to measure a temperature of the gas supplied to the first gas meter,
wherein the first processing circuitry is further configured to derive the first heating value of the gas passing through the first gas meter based on the sound velocity of the gas derived by the first processing circuitry, and (ii) on the temperature of the gas derived by the temperature sensor.

8. A gas meter system according to claim 7, wherein the first processing circuitry is further configured to diagnose whether a present heating value is abnormal based on a transition of the first heating value derived by the first processing circuitry.

9. The gas meter system according to claim 6, wherein the second processing circuitry is further configured to diagnose whether a present heating value is abnormal based on a transition of the first heating value derived by the first processing circuitry.

10. The gas meter system according to claim 2, further comprising a temperature sensor configured to measure a temperature of the gas supplied to the first gas meter,
wherein the first processing circuitry is further configured to derive the first heating value of the gas passing through the first gas meter based (i) on the sound velocity of the gas derived by the first processing circuitry, and (ii) on the temperature of the gas derived by the temperature sensor.

11. The gas meter system according to claim 10, wherein the second processing circuitry is further configured to diagnose whether a present heating value is abnormal based on a transition of the first heating value derived by the first processing circuitry.

12. The gas meter system according to claim 2, wherein the second processing circuitry is further configured to diagnose whether a present heating value is abnormal based on a transition of the first heating value derived by the first processing circuitry.

13. The gas meter system according to claim 1, wherein the gas comprises a hydrocarbon gas.

14. The gas meter system according to claim 13, further comprising a temperature sensor configured to measure a temperature of the gas supplied to the first gas meter,
wherein the first processing circuitry is further configured to derive the first heating value of the gas passing through the first gas meter based (i) on a sound velocity of the gas derived by the first processing circuitry, and (ii) on the temperature of the gas derived by the temperature sensor.

15. A gas meter system according to claim 14, wherein the second processing circuitry is further configured to diagnose whether a present heating value is abnormal based on a transition of the first heating value derived by the first processing circuitry.

16. The gas meter system according to claim 13, wherein the second processing circuitry is further configured to diagnose whether a present heating value is abnormal based on a transition of the first heating value derived by the first processing circuitry.

17. The gas meter system according to claim 1, wherein the second processing circuitry is further configured to diagnose whether a present heating value is abnormal based on a transition of the first heating value derived by the first processing circuitry.

18. A heating value estimation method, comprising:
deriving a first heating value of a gas passing through a first gas meter from a plurality of first gas meters; and
estimating a second heating value of a gas passing through a second gas meter provided separately from the first gas meter based on the first heating value of the gas of the first gas meter that is arranged within a predetermined range with respect to the second gas meter on a gas supply pipe configured to supply the gas,
wherein the first gas meter is a closest gas meter to the second gas meter among the plurality of first gas meters at which the gas passing through the first gas meter is at the same time as the gas passing through the second gas meter.

* * * * *